United States Patent
Gosling et al.

[19]

[11] Patent Number: 5,849,976
[45] Date of Patent: Dec. 15, 1998

[54] MOVING BED SOLID CATALYST HYDROCARBON ALKYLATION PROCESS

[75] Inventors: Christopher David Gosling, Roselle; Daniel L. Weiler, Arlington Heights; Reenen Andre De Villiers, Chicago, all of Ill.

[73] Assignee: UOP LLC, Des Plaines, Ill.

[21] Appl. No.: 641,156

[22] Filed: Apr. 29, 1996

Related U.S. Application Data

[63] Continuation-in-part of Ser. No. 280,959, Jul. 27, 1994, abandoned.

[51] Int. Cl.[6] ........................................... C07C 2/56
[52] U.S. Cl. ............................................... 585/709
[58] Field of Search .................................. 585/709

[56] References Cited

U.S. PATENT DOCUMENTS

| | | | |
|---|---|---|---|
| 3,655,813 | 4/1972 | Kirsch et al. | 260/683.43 |
| 3,838,038 | 9/1974 | Greenwood et al. | 208/108 |
| 3,893,942 | 7/1975 | Yang | 252/411 |
| 3,978,150 | 8/1976 | McWilliams, Jr. | 260/683.3 |
| 4,139,573 | 2/1979 | Carson | 260/683 |
| 5,157,196 | 10/1992 | Crossland et al. | 585/720 |

*Primary Examiner*—Glenn Caldarola
*Assistant Examiner*—In Suk Bullock
*Attorney, Agent, or Firm*—Thomas K. McBride; John F. Spears, Jr.

[57] ABSTRACT

Hydrocarbons are alkylated using slowly moving cylindrical beds of solid catalyst in a process featuring a cooling zone within the reaction zone and a moving bed catalyst regeneration zone. The catalyst passes downward through both zones, which may be stacked upon one another. The reaction zone is operated at liquid-phase conditions, and the catalyst is periodically subjected to a regeneration procedure employing a hydrogen-containing stream. Direct heat exchange within the reaction zone removes the heat of the reaction.

7 Claims, 1 Drawing Sheet

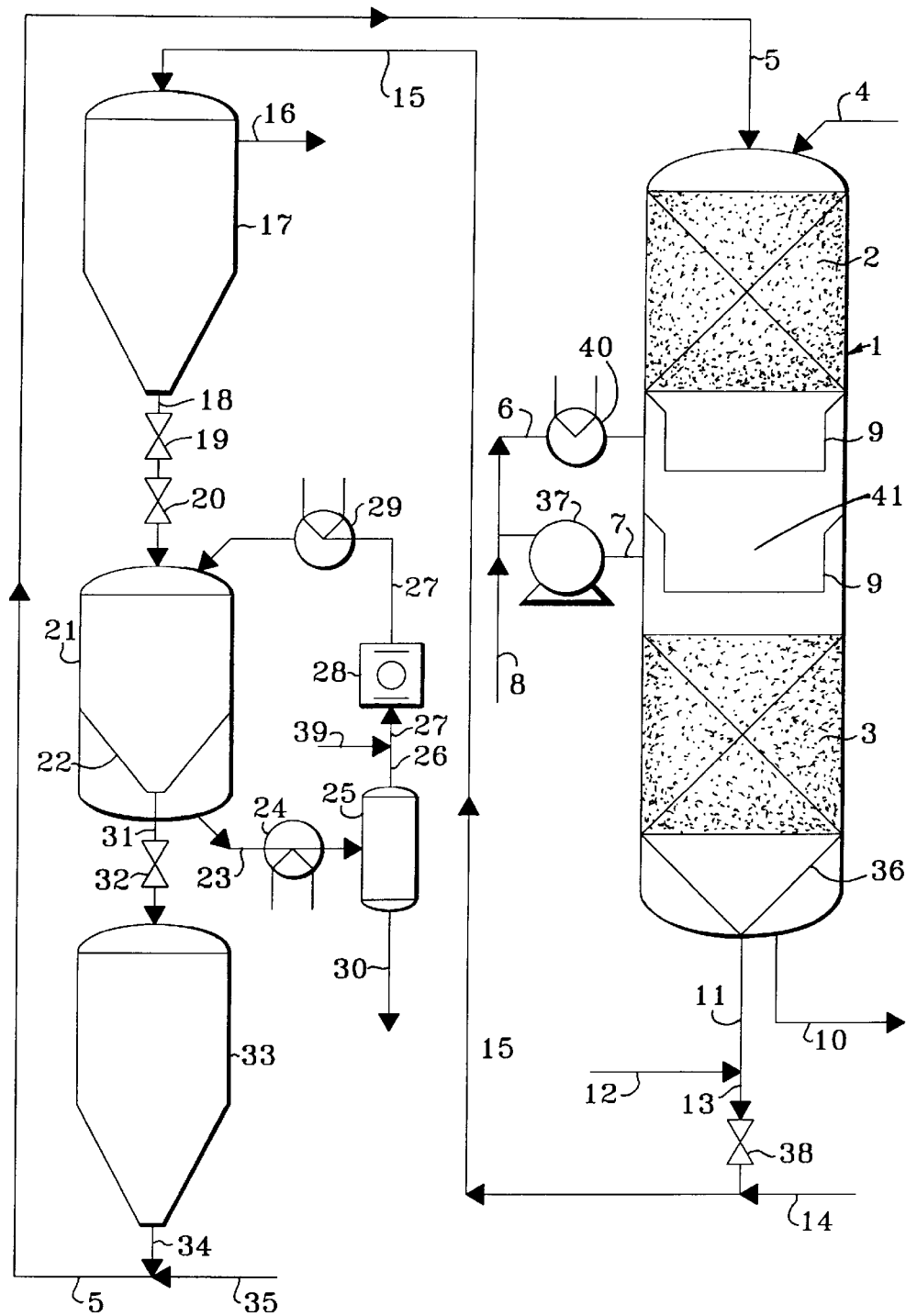

5,849,976

MOVING BED SOLID CATALYST HYDROCARBON ALKYLATION PROCESS

CROSS REFERENCE TO RELATED APPLICATION

This application is a continuation-in-part of our prior application Ser. No. 08/280,959 filed Jul. 27, 1994, now abandoned.

FIELD OF THE INVENTION

The invention relates to a hydrocarbon conversion process. The invention specifically relates to a process for alkylation of hydrocarbons such as aromatics or paraffins to produce useful chemicals and motor fuel using a solid catalyst. The invention is primarily directed to a moving bed process for the solid bed alkylation of isobutane to produce $C_8$ isoparaffins useful as motor fuel blending components.

RELATED ART

Large amounts of high octane gasoline are produced commercially by alkylation of isobutane with butenes or propylene. This significantly increases the value of the $C_4$ feed hydrocarbons. Large amounts of valuable alkyl aromatic hydrocarbons including cumene, ethylbenzene and $C_{10}$–$C_{15}$ linear alkylaromatics are produced by the alkylation of benzene with olefins of the appropriate carbon number.

The variety of possible feed reactants and the passage of time has led to the development of a number of effective alkylation technologies which are employed in large scale commercial facilities. One of the most widely used processes for the production of motor fuel is HF alkylation as described in U.S. Pat. No. 4,139,573 issued to D. B. Carson. This reference provides an overview of the HF alkylation process.

U.S. Pat. No. 3,893,942 issued to C. Yang discloses a method of increasing the stability of zeolitic alkylation catalysts by including a Group VIII metal hydrogenation agent and periodically hydrogenating deposits on partially deactivated catalyst by contact with a hydrogen containing gas.

A design for a solid catalyst alkylation process is described in U.S. Pat. No. 5,157,196. This process uses a moving bed of catalyst, with the catalyst being loaded with a paraffin substrate outside of the reactor and then passed through the reactor and into a product recovery zone to produce motor fuel alkylate.

U.S. Pat. No. 3,655,813 issued to F. W. Kirsch et al. discloses a continuous solid catalyst alkylation process. This liquid phase reaction apparently occurs in a stirred tank reactor, with a slip stream containing reactants and the catalyst being removed for transfer into a regeneration zone. The separated spent catalyst is regenerated by combustion of carbonaceous deposits.

The use of moving beds of a solid catalyst which is cycled between reaction and regeneration zones is described in U.S. Pat. No. 3,838,038 issued to A. R. Greenwood. Subsequent references have taught the extension of this moving bed technology to other vapor phase reactions such as dehydrogenation as disclosed in U.S. Pat. No. 3,978,150 issued to F. G. McWilliams. In such processes interstage heaters are employed to reheat flowing reactants after the reactants have been separated from the catalyst.

BRIEF SUMMARY OF THE INVENTION

The invention is a solid catalyst alkylation process in which the catalyst is slowly moved through reaction, cooling and regeneration zones to provide continuous uniform operation. The invention is also characterized by a unique method of interstage cooling employed to maintain the desired reaction zone operating temperature.

One broad embodiment of the invention may be characterized as a process for the alkylation of a feed hydrocarbon in a moving bed reaction zone which comprises the steps: passing a feed hydrocarbon and an alkylating agent into a moving bed reaction zone containing a first catalyst bed and a second catalyst bed which are operated at alkylation-promoting conditions and separated by an intermediate catalyst filled cooling zone, and reacting the feed hydrocarbon and the alkylating agent to produce a product hydrocarbon; passing the catalyst and the hydrocarbons exiting the first catalyst bed downward together through the cooling zone into the second catalyst bed; cooling the catalyst moving downward through the cooling zone by direct heat exchange against circulating hydrocarbons which have been cooled at a point outside the reaction zone; withdrawing a process stream comprising said feed hydrocarbon and said product hydrocarbon, from the reaction zone and recovering the product hydrocarbon; periodically removing a quantity of used catalyst from a lower end of the reaction zone and passing said catalyst into an upper end of a regeneration zone; contacting the used catalyst present in the regeneration zone with a regeneration media comprising hydrogen at regeneration conditions and thereby producing regenerated catalyst; and, transferring regenerated catalyst removed from a lower end of the regeneration zone into an upper end of the reaction zone.

BRIEF SUMMARY OF THE DRAWING

The drawing is a simplified diagram of a moving bed alkylation unit for the production of motor fuel employing a reaction zone 1, which contains a cooling zone 41, and catalyst regeneration zone 21.

DETAILED DESCRIPTION AND PREFERRED EMBODIMENTS

As previously stated, hydrocarbon alkylation is widely used in the petroleum refining and petrochemical industries to produce a variety of useful acyclic and cyclic hydrocarbon products used as motor fuel, plastic and detergent precursors and petrochemical feedstocks. Much of the installed base of alkylation capacity uses liquid phase hydrofluoric acid, generally referred to as HF, as the catalyst. The petroleum industry continues to use HF acid as the alkylation catalyst of choice due to the high octane fuel it produces together with other operational advantages. The use of HF in these applications has a long record of highly dependable and safe operation. However, the potential damage from an unintentional release of any sizeable quantity of HF and the need to safely dispose of some by-products formed in product or effluent treating procedures has led to an increasing demand for alkylation process technology which does not employ HF as the catalyst.

It is an objective of this invention to provide a commercially viable alkylation process which does not employ liquid phase HF as the catalyst. It is a further objective of the subject process to provide an alkylation process which counteracts the relatively quick deactivation of the currently available solid motor fuel alkylation catalysts. It is a specific objective of the invention to provide a solid bed motor fuel alkylation process for the production of $C_8$ isoparaffins.

The subject invention achieves these objectives by the use of a unique flow scheme that employs a "moving bed" of catalyst in both the reaction and the regeneration zones to provide a continuous level of performance. The use of this reactor configuration also has the advantage of reducing both the catalyst and liquid hydrocarbon inventory in the plant, which are desirable cost and safety benefits. The use of a system which actually transfers the catalyst between reaction and regeneration zones has the further benefit of allowing the catalyst to be partially or totally replaced without disrupting the operation of the process.

The preferred feed hydrocarbon to the subject process is isobutane, which is then reacted with one or more butenes to produce a $C_8$ alkylate for use as gasoline boiling range motor fuel. The feed hydrocarbon or hydrocarbon substrate in this instance may vary to include other hydrocarbons including $C_5$ or $C_6$ paraffins. Another preferred feed hydrocarbon is benzene, which may be alkylated with a wide range of feed olefins including ethylene, propylene and butylene to produce such chemicals as ethylbenzene and cumene. A large amount of benzene is also alkylated with higher carbon number olefins having from about ten to about fifteen carbon atoms per molecule to produce linear alkylbenzenes which are then sulfonated to produce detergents. The alkylating agent which may be chosen from a variety of compounds including monohydric alcohols and olefins. Examples of alcohols which may be employed as the alkylating agent include ethanol and methanol. Methanol, for instance, is widely described in the literature as being useful in the para selective methylation of benzene and toluene. Preferred feed olefins have from three to five carbon atoms per molecule, with propylene and normal butene being preferred for motor fuel alkylation.

The catalyst used in the process is preferably retained in one or more cylindrical fixed (nonfluidized) beds in a vertical reaction zone. The reactant flow through the catalyst bed is preferably in a vertical, preferably downward, direction but could be horizontal if the catalyst is retained in an annular radial flow catalyst bed. The reaction zone should be provided with an effective means to distribute the entering liquid reactants over and through the entire bed of catalyst in a highly uniform manner and to maintain uniform flow across the entire cross-section of the bed as the liquid passes downward. The requirement to move the catalyst makes the use of most intrabed fluid collection and redistribution devices impractical and emphasis must be placed on proper feed addition and removal from the bed to counteract maldistribution.

The overall process flow of the subject invention is best described by reference to the Drawing. The Drawing is a simplified depiction of the motor fuel alkylation embodiment of the invention in which a liquid-phase feed stream comprising normal butenes and isobutane from line 4 is passed into the upper end of the reaction zone 1. These reactants-then pass downward through a cylindrical upper bed 2 of solid alkylation catalyst, which results in the reaction of some of the entering isobutane with substantially all of the butenes and the production of branched $C_8$ isoparaffinic product hydrocarbons. The catalyst in this bed is not fluidized and rests on catalyst below it. As the alkylation reaction is very exothermic the released heat of reaction will cause some increase in the temperature of the reactant stream and the catalyst. The presence of a large excess quantity of the feed hydrocarbon is therefore desirable to provide a heat sink. An excess of the feed hydrocarbon is also desired to minimize polymerization of the olefin and produce a high quality alkylate.

The effluent stream of the upper catalyst bed comprises residual isobutane, $C_8$ alkylate product and any residual butenes proceeds downward into a cooling zone 41 comprising this single cylindrical passageway. In the cooling zone a portion of the liquid-phase reactants are withdrawn through line 7 by means of pump 37. The withdrawn reactants are then passed into line 6 and through an indirect heat exchanger 40 used to cool the reactants. The cooled reactants are then returned to the cooling zone. This cools the larger total reactant stream passing downward through the cooling zone and the rest of the reaction zone. It of course also cools the catalyst by direct heat exchange. This cooling of the circulating reactants is sufficient to lower the temperature of the reactants and the catalyst which is passing through the cooling zone and thus must be sufficient to both cool these materials and remove any heat of reaction released from alkylation performed in the cooling zone. Such alkylation results due to the preferred addition of additional butenes through line 8. This split addition of the olefin is intended to provide a higher overall isobutane to olefin ratio than would occur if all the olefin is added at the reactor inlet. The cooling zone therefore also functions to thoroughly admix the newly added olefin into the much larger reactant flow. Both the withdrawal and return of the reactants are facilitated by the use of annular flow distribution scallops or shrouds 9.

After leaving the cooling zone 41 the reactants continue to flow downward through a lower second cylindrical catalyst bed 3 in which additional alkylate is produced. Finally at the bottom end of the reaction zone 1 the reactants are separated from the catalyst as they pass out of the catalyst via a cone shaped porous screen 36. The remaining reactants and the product alkylate are then withdrawn from the process in line 10 and passed into a product recovery zone not shown. The product recovery zone will normally comprise at least one fractionation column operated in a manner which recovers isobutane for recycling to the reaction zone. This product recovery zone may be of conventional design.

The catalyst at all levels in the overall reaction zone 1 gradually moves downward by the action of gravity as small amounts of catalyst are periodically removed from the bottom of the reaction zone via line 11. The porous tapered funnel-like catalyst support 36 or a number of evenly spaced catalyst collectors is used to remove catalyst from the lower catalyst bed. It is preferred that the catalyst leaving the bottom of the reactor is flushed free of olefin and reaction products by an upward flowing stream of isobutane charged through line 12 and then passed upward into the reaction zone. This isobutane will leave the reaction zone with the product stream of line 10.

Periodically small quantities of used catalyst are allowed to pass downward through lines 11 and 13. A valve 38 or a series of valves can be used in conjunction with the upward flow of isobutane to control this flow of catalyst. The catalyst drained from the reaction zone is then transferred, using liquid phase isobutane from line 14, through line 15 into a lock hopper 17. The catalyst falls into the lock hopper with the isobutane transfer liquid exiting via line 16. Periodically used catalyst is transferred downward through line 18 and valves 19 and 20 into the regeneration zone 21. The used catalyst is suspended on a cone shaped porous grid 22 which allows free liquid to drain off the catalyst and then be removed via line 23. The catalyst is then contacted with a vapor phase admixture of hydrogen and isobutane. It is preferred to employ a regeneration gas comprising isobutane because of the higher heat capacity of isobutane compared to hydrogen. This allows for faster heating of the catalyst during regeneration. This mixture enters the top of the regeneration zone 21 through line 27 and passes downward through the catalyst before exiting in line 23. The gas mixture is cooled as needed in heat exchanger 24 to condense isobutane and then passed into the vapor-liquid separation zone 25. The isobutane condensate is collected and withdrawn as needed via line 30. This is to balance isobutane entering with the wet catalyst and also removes heavy hydrocarbons. The uncondensed vapor is removed in line 26 and passed via line 27 through a compressor 28 which recirculates the gas through a heater 29 and the catalyst bed in the regeneration zone. As needed hydrogen is passed into the loop via line 39 to maintain the composition of the circulating gas at approximately 50 percent hydrogen. The regeneration zone cycle should be completed in from about 15 to about 60 minutes time at a temperature of about 100 to about 400 degrees Fahrenheit. This procedure is normally sufficient to regenerate the preferred catalyst sufficiently that it may be returned to the reaction zone.

The mass of regenerated catalyst in the regeneration zone 21 is then completely transferred into a second lock hopper 33 via line 31 and valve 32. This is a total transfer as compared to the smaller incremental transfers used to remove catalyst from the reaction zone 1. Quantities of the regenerated catalyst are periodically removed in line 34 and transferred through line 5 with liquid phase isobutane from line 35. The regenerated catalyst then flows into the top of the reaction zone and falls to the top of the cylindrical bed of catalyst in use in this zone.

As used herein the term "rich" is intended to indicate a concentration of the indicated compound or class of compounds greater than 50 mole percent and preferably greater than 70 percent.

The fractional distillation column(s) used as the product recovery zone is preferably operated at conditions effective to separate the entering hydrocarbons into a net overhead stream which is rich in propane and a net bottoms stream which is rich in the $C_8$ product hydrocarbon. Also normally removed from this column, which is referred to in the art as an isostripper, are a sidecut stream comprising most of the normal butane which enters the process in the feed streams and a normally vapor phase sidecut stream, which is rich in isobutane. The isobutane sidecut stream is preferably recycled to the reaction zone.

It is postulated that a significant portion of the deactivation seen in solid bed alkylation catalysts results from the reaction of the feed olefin(s) to form dimers, trimers or even heavier polymeric entities which block catalyst pores and/or catalyst reactive sites. Additionally, these olefins can react further to form diolefinic and cyclic compounds which are found as by-products in liquid phase alkylation. These materials are a portion of what is commonly called acid soluble oil (ASO). Deposition of these materials on the catalyst will cause rapid deactivation. In order to counteract this mode of deactivation, it is preferred to use an alkylation catalyst which has a weak hydrogenation function which is selective for the hydrogenation of the olefinic dimers and other olefinic "heavy" compounds produced on the catalyst. The use of such a catalyst is however not necessary for the performance of the subject process.

The presence of an active metal hydrogenation component on the catalyst will cause any hydrogen which enters the reaction zone to hydrogenate a feed olefin. This tendency may be counteracted through the composition of the catalyst but is preferably totally avoided by preventing the entrance of hydrogen into the reaction zone from the regeneration zone through the use of suitable isolation methods.

Either vapor phase or liquid phase regeneration may be employed. In both instances the catalyst is contacted with hydrogen to effect olefin hydrogenation. Previously it was felt vapor phase regeneration was necessary and it is still preferred, but recent advances set out below allow liquid-phase regeneration. Liquid-phase regeneration is desired as it simplifies the mechanical design of the process and eliminates a need to switch between handling of wet and dry solids. The exact method of catalyst regeneration does not form a limitation of the regeneration step in the subject process. Regeneration is expected to include a periodic "washing" of the catalyst with a liquid phase hydrocarbon such as isobutane or benzene, possibly at an elevated temperature and in the presence of some hydrogen to remove carbonaceous deposits. The catalyst may also, if necessary, be periodically contacted with a combustion supporting gas such as air, nitrogen-diluted air or ozone to oxidize the carbonaceous deposits which cannot be removed by contact with a liquid phase hydrocarbon and/or a vapor-phase hydrogen stream, but this procedure is not preferred.

It is desired to employ a hydrocarbon already present in the process as any hydrocarbon used during regeneration. Of the hydrocarbons available in the process, a stream which is rich in $C_4$ hydrocarbons and has a low concentration of olefins and product hydrocarbons is preferred. Any washing step occurs before the hot hydrogen stripping step. Some alkylation catalysts may have isomerization activity, especially at higher regeneration temperatures. In that instance normal butane would be a preferred regenerant as the catalyst would convert some normal butane into isobutane, a valuable process feed material. The liquid phase wash step is performed at a temperature of 100° to 270° F. for about 10 to about 90 minutes.

The liquid-phase regeneration of the used catalyst may be performed using either a liquid-phase mild regeneration zone or a high temperature liquid-phase regeneration zone or both in series or in parallel. Both require hydrogen addition. A mild regeneration zone is capable of performing only a partial regeneration of the catalyst as by removing surface deposits soluble in the feed hydrocarbon and performing some hydrogenation. The high temperature regeneration zone performs a complete hydrogenative regeneration requiring a minimum stoichiometric amount of hydrogen. This regeneration restores essentially all activity to the used catalyst.

The amount of hydrogen charged to a high temperature liquid phase regeneration zone must be at least equal to the stoichiometrically required amount for the hydrogenation of the carbonaceous material present on the used catalyst entering the particular regeneration zone. For purposes of this calculation, it is assumed that the carbonaceous material is composed of monoolefinic octenes. The amount of hydrogen required for regeneration will therefore vary with the catalyst condition but can be easily calculated and controlled. An additional quantity of hydrogen, again equal to the stoichiometrically required amount, is charged to any low temperature regeneration zone used in the process. The regeneration performed in the low temperature regeneration zone is only capable of recovering about 90–95 percent of the activity of the preferred catalyst after use for motor fuel alkylation, which results in significant deactivation after a number of catalyst passes through the reaction zone. The regeneration in the high temperature regeneration zone will recover close to 100 percent of the catalyst's activity. Different results may be obtained for different catalysts.

The average residence of catalyst particles in this liquid-phase hydrocarbon regeneration zone is preferably from about 0.5 to 20 minutes. The liquid-phase low temperature or mild regeneration may be performed in a vessel or conduit in relatively open communication with the reaction zone. The temperature and pressure conditions employed in this instance are therefore very similar to those in the reaction zone. The temperature in the low temperature regeneration zone will correspond to the outlet temperature of the reactor, with any required cooling being performed downstream of the regeneration zone. The temperature of the feed stream can be used to reduce the temperature of the regenerated catalyst. Further information on the regeneration of the preferred catalyst and the catalyst itself may be obtained from U.S. Pat. Nos. 5,310,713 and 5,391,527.

All of the used catalyst may alternatively be regenerated in a high temperature liquid-phase regeneration zone. Preferably some catalyst is treated in each type of liquid-phase regeneration zone. The flow rate through the high temperature regeneration zone need be only about 0.2 to about 30 weight percent, and preferably from about 10 to about 20 weight percent of the total catalyst removed from the reaction zone.

In contrast to the low temperature regeneration zone, the high temperature regeneration zone is operated at conditions independent from the reaction zone. The pressure in the high temperature regeneration zone is preferably substantially the same as in the rest of the process, with minor differences being caused by differing elevations and flow induced pressure drops. In the case of motor fuel alkylation the maximum temperature in the high temperature regeneration zone will be set by the critical temperature of the feed hydrocarbon. For motor fuel alkylation using butanes, this results in a maximum operating temperature of about 270° F. The combination of pressure and temperature are controlled to avoid the presence of two phase conditions. That is, no vapor should be present in this or any other part of the process (except a vapor-phase regeneration zone), and it is presently preferred to avoid supercritical conditions even though this may be considered a single phase. The average temperature in the high temperature regeneration zone should be at least 50 degrees (F.) above the outlet temperature of the reaction zone and is preferably 70–150 degrees higher.

A preferred vapor phase regeneration method is described above. It may proceed for up to 12 to 24 hours, with part of this time being used in drying, heating and then cooling the catalyst. Higher temperatures up to 525° F. may be needed for a total broad temperature range of about 100° to 525° F. The pressure may be dictated by the general operation of the process.

One embodiment of the invention may accordingly be characterized as a moving bed process for the alkylation of a feed hydrocarbon which comprises the steps: passing a feed hydrocarbon and an alkylating agent into a liquid-phase moving bed reaction zone containing a first bed and a second bed of solid alkylation catalyst operated at alkylation-promoting conditions and separated by an intermediate catalyst filled cooling zone, and reacting the feed hydrocarbon and the alkylating agent to produce a product hydrocarbon; passing all of the catalyst and substantially all of the reactants exiting the first catalyst bed downward through the cooling zone into the second catalyst bed; cooling the catalyst moving downward through the cooling zone by direct heat exchange against circulating reactants which have been cooled at a point outside the reaction zone; passing a process stream comprising said feed hydrocarbon and said product hydrocarbon, and which is withdrawn from the reaction zone, into a product recovery zone, and recovering the product hydrocarbon; periodically removing a quantity of used catalyst from a lower end of the reaction zone and passing said catalyst into an upper end of a regeneration zone; contacting the used catalyst present in the regeneration zone with a regeneration media comprising hydrogen at regeneration conditions and thereby producing regenerated catalyst; and, transferring regenerated catalyst removed from a lower end of the regeneration zone into an upper end of the reaction zone.

A preferred embodiment of the subject invention can accordingly be characterized as a process for the alkylation of a feed isoparaffin which comprises the steps: passing a feed stream comprising a $C_3$–$C_5$ isoparaffinic hydrocarbon and a $C_3$–$C_5$ olefinic hydrocarbon downward through a reaction zone containing two or more cylindrical beds of a solid alkylation catalyst, with the cylindrical beds of catalyst being separated by a catalyst-filled cooling zone, which cooling zone comprises a single cylindrical passageway through which all of the catalyst and reactants pass in cocurrent flow and in which all of the catalyst is cooled by direct heat exchange against recirculated hydrocarbons flowing downward through the catalyst located in the cylindrical passageway with the reaction zone operated at liquid-phase alkylation-promoting conditions and reacting the isoparaffinic hydrocarbon and the olefinic hydrocarbon to produce a branched paraffinic product hydrocarbon; removing an effluent stream comprising said feed hydrocarbon and said product hydrocarbon from a lower end of the reaction zone, and passing the effluent stream into a product recovery zone, and recovering the product hydrocarbon; periodically removing a quantity of used catalyst from a lower end of the reaction zone, causing catalyst to travel downward through the cooling zone, and passing said used catalyst into an upper end of a moving bed regeneration zone located above the reaction zone; contacting a bed of used catalyst present in the regeneration zone with a regeneration media comprising hydrogen at regeneration conditions and thereby producing regenerated catalyst; and, periodically transferring quantities of regenerated catalyst downward from the regeneration zone into the reaction zone.

The subject process can be performed using any solid or heterogeneous catalyst which is relatively stable at the conditions maintained in the reactor and has the required activity and selectivity for the desired reaction. The catalyst should be spherical as this promotes easier catalyst movement in the reaction and regeneration zones and transfer lines. Other shapes such as pellets or extrudates with length:diameter ratios close to one can also be used. The catalyst must be physically strong enough to withstand being transferred through the system without significant breakage.

A large number of alkylation catalysts have been proposed for the production of motor fuel including various zeolites and superacid catalysts. For instance, U.S. Pat. No. 4,384,161 describes the use of a large pore zeolite and a Lewis acid. The zeolites referred to include ZSM-4, ZSM-3, and the faujasites including zeolite Y and mordenite. The Lewis acids mentioned in this reference include boron trifluoride and aluminum chloride. The alkylation of isoparaffins using a somewhat similar catalyst system comprising a large pore crystalline molecular sieve such as a pillared silicate or an aluminophosphate or silicoaluminophosphate together with a gaseous Lewis acid is disclosed in U.S. Pat. No. 4,935,577. The use of these Lewis acids is not preferred in the subject process as they provide their own waste handling and safety problems. They also will probably require provisions for the circulation of the Lewis acid, which may complicate the process as shown by the just cited U.S. Pat. No. 4,935,577. U.S. Pat. No. 4,377,721 describes the use of ZSM-20 as a motor fuel alkylation catalyst. U.S.

Pat. No. 5,157,200 describes an isoparaffin alkylation process using a catalyst comprising a crystalline transition alumina, preferably eta or gamma alumina, which has been treated with a Lewis acid under anhydrous conditions. Previously referred to U.S. Pat. No. 5,157,196 describes an isoparaffin alkylation process using a slurried solid catalyst, with the preferred catalyst being an acid washed silica which has been treated with antimony pentafluoride. Both of these last two references describe a number of prior art solid bed paraffin alkylation catalysts.

Silicalites have been described as useful alkylation catalysts for the production of monoalkylbenzenes in U.S. Pat. No. 4,489,214 to J. R. Butler et al. and as useful in methylating toluene to produce paraxylene in U.S. Pat. No. 4,444,989 assigned to F. E. Herkes. The use of ZSM-5 zeolites in aromatic alkylation is described in U.S. Pat. No. 3,751,506. ZSM-5 zeolites that have been treated with one or more compounds or elements to improve their selectivity for para-selective alkylation of aromatic hydrocarbons are described in U.S. Pat. No. 4,420,418. The use of zeolite L, zeolite Omega and zeolite beta as alkylation catalysts for the selective alkylation of benzene is described in U.S. Pat. No. 4,301,316. The use of a number of natural and synthetic zeolites including clinoptilolite and zeolite Y is described in U.S. Pat. No. 3,251,897. These references give guidance in both the composition and usage of the catalysts.

A preferred paraffin alkylation catalyst comprises a refractory inorganic oxide impregnated with a monovalent cation, especially an alkali metal cation or an alkaline earth metal cation, and whose bound surface hydroxyl groups have been at least partially reacted with a Friedel-Crafts metal halide. Isomerization analogs of these catalysts without the monovalent metal cations are described in U.S. Pat. Nos. 2,999,074 and 3,318,820 which describe preparation techniques which can be applied to the preferred catalysts. The refractory oxide is preferably alumina having a surface area greater than 50 $m^2/g$, but the use of other oxides including titania, zirconia, silica, boria and aluminum phosphate is contemplated. The preferred catalyst also contains a metal component active for olefin hydrogenation deposited on the inorganic oxide prior to reaction of the bound surface hydroxyl groups with metal halides. This metal may be chosen from the group consisting of nickel, platinum, palladium, rhenium, and ruthenium with the first four of these metals being preferred. The one or more monovalent metal or alkaline earth metal cations in the catalyst may be selected from the group consisting of lithium, sodium, potassium, cesium, silver, copper, beryllium, magnesium, calcium and barium. The use of potassium to reduce the acidity of the catalyst is preferred. Subsequent to the deposition of these metals and the controlled calcination of the composite the composite is reacted with a Friedel-Crafts metal halide. The metal of the halide may be aluminum, zirconium, tin, tantalum, gallium, antimony or boron. Suitable halides are the fluorides, chlorides and bromides.

Alkylation conditions suitable for use in the reaction zone of the subject process with the preferred catalyst include an outlet temperature of about −17 to about 70 degrees C., preferably 10 to 38 degrees C., and a pressure as required to maintain at least a major portion (greater than 50 moles) of the feed hydrocarbon present as a liquid. These outlet temperatures assume an approximate 20–50 F. degree temperature rise through the catalyst bed which depends greatly on such factors as the amount of olefin in the feed stream. A moderately elevated pressure above that required to maintain liquid phase operation in the general range of about 1380 to about 6500 kPa (200–950 psig) is preferred. Preferably all of the reactants are present in the liquid phase. The olefin weight hourly space velocity (WHSV) should be less than 2.0 $hr^{-1}$ and preferably from about 0.1 to about 1.0.

It has recently been determined that operation of the reaction zone at higher pressures results in increased catalyst activity. This observation was derived from operations performed at higher pressures intended to promote an increase in the amount of hydrogen dissolved in the liquid-phase hydrocarbon used to regenerate the catalyst. The increased cost of high pressure equipment and operations dictate a limit to pressure increases to increase catalyst performance but a pressure above 400 psig is desirable. A pressure in the general range of 100–500 psig is preferred.

It is generally preferred that the process is operated without any free hydrogen being present in the reaction zone. It is also preferred to maintain an excess of the feed hydrocarbon compared to the alkylating agent. That is, it is preferred to operate with a ratio of the feed hydrocarbon to a feed alkylating agent greater than 2:1, and preferably from about 5:1 to about 20:1 as measured by the flow rates into the reaction zone. Specifically, it is preferred that the molar ratio of isoparaffin to olefin being charged to the reaction zone is greater than 2:1 and more preferably greater than 7:1. Higher ratios up to 100:1 are contemplated as being desirable for longer catalyst life between regenerations.

What is claimed:

1. A process for the alkylation of a feed hydrocarbon which comprises the steps:

(a) passing a paraffinic hydrocarbon and an olefinic hydrocarbon into the upper end of a reaction zone containing at least two beds of solid alkylation catalyst which are separated by an intermediate catalyst filled cooling zone and operated at liquid-phase alkylation-promoting conditions, and reacting the paraffinic hydrocarbon and the olefinic hydrocarbon agent to produce a product hydrocarbon, with catalyst passing downward from an upper catalyst bed to a lower catalyst bed while being cooled in the cooling zone by direct heat exchange against externally cooled liquid-phase reactants;

(b) passing an effluent stream comprising said paraffinic hydrocarbon and said product hydrocarbon, and which is withdrawn from the reaction zone, into a product recovery zone, and recovering the product hydrocarbon;

(c) periodically removing a quantity of used catalyst from a lower end of the reaction zone and passing said catalyst into an upper end of a regeneration zone;

(d) contacting the used catalyst present in the regeneration zone with a regeneration media comprising hydrogen at regeneration conditions and thereby producing regenerated catalyst; and, (e) transferring regenerated catalyst from the regeneration zone into the reaction zone.

2. The process of claim 1 further characterized in that a process stream comprising the olefinic hydrocarbon is passed into the cooling zone and admixed with a stream of liquid phase cooling media circulated through catalyst retained in the cooling zone.

3. The process of claim 2 further characterized in that the paraffinic hydrocarbon is isobutane or isopentane.

4. A process for the alkylation of a feed isoparaffin which comprises the steps:

(a) passing a feed stream comprising a $C_3$–$C_5$ isoparaffinic hydrocarbon and a $C_3$–$C_5$ olefinic hydrocarbon downward through a reaction zone containing two or more cylindrical beds of a solid alkylation catalyst, with the cylindrical beds of catalyst being separated by a catalyst-filled cooling zone, which cooling zone comprises a single cylindrical passageway through which all of the catalyst and reactants pass in cocurrent flow and in which all of the catalyst is cooled by direct heat exchange against recirculated hydrocarbons flowing downward through the catalyst located in the cylindrical passageway with the reaction zone operated at liquid-phase alkylation-promoting conditions and reacting the isoparaffinic hydrocarbon and the olefinic hydrocarbon to produce a branched paraffinic product hydrocarbon;

(b) removing an effluent stream comprising said feed hydrocarbon and said product hydrocarbon from a lower end of the reaction zone, and passing the effluent stream into a product recovery zone, and recovering the product hydrocarbon;

(c) periodically removing a quantity of used catalyst from a lower end of the reaction zone, causing catalyst to travel downward through the cooling zone, and passing said used catalyst into an upper end of a moving bed regeneration zone located above the reaction zone;

(d) contacting a bed of used catalyst present in the regeneration zone with a regeneration media comprising hydrogen at regeneration conditions and thereby producing regenerated catalyst; and, (e) periodically transferring quantities of regenerated catalyst downward from the regeneration zone into the reaction zone.

5. The process of claim 4 further characterized in that the alkylation catalyst comprises a metal component having hydrogenation activity.

6. The process of claim 4 further characterized in that a liquid-phase first process stream comprising only a portion of the hydrocarbons flowing through the reaction zone and including the product hydrocarbon is removed from the cooling zone, cooled by indirect heat exchange and then returned to the cooling zone.

7. The process of claim 6 further characterized in that a liquid phase second process stream comprising the olefinic hydrocarbon is passed into the cooling zone, and that alkylation is performed in the cooling zone.

* * * * *